US00PP11779P2

(12) United States Plant Patent
Bergman

(10) Patent No.: US PP11,779 P2
(45) Date of Patent: Feb. 13, 2001

(54) HIBISCUS PLANT NAMED 'CAROLINE'

(75) Inventor: Wendy R. Bergman, Lehigh Acres, FL (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/333,129

(22) Filed: Jun. 14, 1999

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Caroline', characterized by its glossy, undulate, very dary green leaves, upright, outwardly spreading, uniform, dense and symmetrical plant habit that is appropriate for container production; very freely flowering; numerous orange-colored flowers; good resistance to flower bud abscission; and excellent postproduction longevity.

2 Drawing Sheets

BACKGROUND OF THE INVENTION

The present invention relates to a new and distinct cultivar of Hibiscus, botanically known as *Hibiscus rosa-sinensis*, and hereinafter referred to by the cultivar name Caroline.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, resistance to flower bud abscission, and good postproduction longevity.

The new Hibiscus originated from a cross made by the Inventor in Alva, Fla., of a proprietary *Hibiscus rosa-sinensis* selection, designated as code number YB-0602, as the female, or seed, parent with a proprietary *Hibiscus rosa-sinensis* selection, designated as code number YB-1340, as the male, or pollen, parent. The cultivar Caroline was discovered and selected by the Inventor as a flowering plant within the progeny of the stated cross in a controlled environment in Alva, Fla., on Sep. 13, 1995.

Compared to plants of the female parent, the proprietary Hibiscus selection code number YB-0602, plants of the new Hibiscus are more compact; have slightly glossier leaves; and have lighter and brighter flower color. In addition, flowers of plants of the new Hibiscus do not have the contrasting "eye" color, however flowers of plants of the female parent have strong pink-colored "eyes". Plants of new Hibiscus have slightly lighter green and less glossy foliage; produce more flowers per day per plant; have smaller flowers; flower about one week later; and differ in flower color when compared to plants of the male parent, the proprietary Hibiscus selection code number YB-1340.

Asexual reproduction of the new Hibiscus by terminal cuttings taken in a controlled environment in Alva, Fla., has shown that the unique features of this new Hibiscus are stable and reproduced true to type in successive generations.

SUMMARY OF THE INVENTION

The cultivar Caroline has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Caroline'. These characteristics in combination distinguish 'Caroline' as a new and distinct cultivar:

1. Glossy, undulate, very dark green leaves.
2. Upright, outwardly spreading, uniform, dense and symmetrical plant habit that is appropriate for container production.
3. Very freely flowering, numerous orance-colored flowers.
4. Good resistance to flower bud abscission.
5. Excellent postproduction longevity.

Plants of the new Hibiscus can be compared to plants of the cultivar Mango Breeze, disclosed in U.S. Plant Pat. No. 11,027. However, in side-by-side comparisons conducted in Alva, Fla., plants of the new Hibiscus differ from plants of the cultivar Mango Breeze in the following characteristics:

1. Plants of the new Hibiscus are slightly more vigorous than plants of the cultivar Mango Breeze.
2. Flower color of plants of the new Hibiscus is brighter and more intense orange compared to flower color of plants of the cultivar Mango Breeze.
3. Flower margins of plants of the new Hibiscus are not as heavily ruffled as flower margins of plants of the cultivar Mango Breeze.

Plants of the new Hibiscus can also be compared to plants of the cultivar Desert Wind, disclosed in U.S. Plant Pat. No. 10,941. However, in side-by-side comparisons conducted in Alva, Fla., plants of the new Hibiscus differ from plants of the cultivar Desert Wind in the following characteristics:

1. Plants of the new Hibiscus are not as outwardly spreading as plants of the cultivar Desert Wind.
2. Plants of the new Hibiscus have slightly lighter green foliage than plants of the cultivar Desert Wind.
3. Plants of the new Hibiscus have smaller flowers than plants of the cultivar Desert Wind.
4. Flower color of plants of the new Hibiscus is much brighter and more intense orange than flower color of plants of the cultivar Desert Wind.

5. Plants of the new Hibiscus flower about one week earlier than plants of the cultivar Desert Wind.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type.

The photograph on the first sheet comprises a side perspective view of a typical plant of 'Caroline'. Both photographs were taken when plants were about 7 months old.

The photograph on the second sheet comprises a close-up view of a typical flower of 'Caroline'. Flower and foliage colors in the photographs may appear different from the actual colors due to light reflectance.

DETAILED BOTANICAL DESCRIPTION

The following observations, measurements and values describe plants grown in Alva, Fla., with five plants per 16.5-cm containers in polyethylene-covered greenhouses, during the late spring under conditions which closely approximate commercial production. Night temperatures ranged between 13 to 24 degrees centigrade. Day temperatures ranged between 21 and 32 degrees centigrade. Plants were about 7 months old when descriptions were taken. In the description, color references are made to The Royal Horticultural Society Color Chart except where general terms of ordinary dictionary significance are used.

Botanical classification: *Hibiscus rosa-sinensis* cultivar Caroline.

Parentage:

*Female or seed parent.*—*Hibiscus rosa-sinensis* proprietary selection designated as code number YB-0602.

*Male or pollen parent.*—*Hibiscus rosa-sinensis* proprietary selection designated as code number YB-1340.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, uniform, dense and symmetrical plant habit.

*Branching habit.*—Freely branching, usually about three or four lateral branches develop after removal of terminal apex.

*Plant height, soil level to top of flowers.*—About 34 cm.

*Plant diameter, area of spread.*—About 40 cm.

*Lateral branch description.*—Length: About 24 cm. Diameter: About 7 mm. Texture: Immature, smooth; mature, woody and rough. Color: Immature: Green, 146A. Mature: Gray, 197A to 197B.

Foliage description:

*Arrangement.*—Alternate, single; numerous; symmetrical.

*Length.*—About 7.75 cm.

*Width.*—About 7.2 cm.

*Shape.*—Broadly ovate.

*Apex.*—Acute.

*Base.*—Obtuse to slightly cordate.

*Margin.*—Serrate to crenate.

*Aspect.*—Undulate.

*Texture.*—Glabrous and glossy on both surfaces.

*Color.*—Young foliage, upper surface: Darker than 146A. Young foliage, lower surface: Close to 146A. Mature foliage, upper surface: Much darker than 147A. Mature foliage, lower surface: Much darker than 147B.

*Petiole.*—Length: About 2.8 cm. Diameter: About 3 mm. Texture: Mostly smooth with very fine pubescence on upper surface. Color: Upper surface: 147A. Lower surface: 146A.

Flower description:

*Natural flowering season.*—Usually spring and summer or during periods of warm weather.

*Flower arrangement.*—Flowers arranged singly at terminal leaf axils. Very freely flowering with usually about three or four flower buds and/or open flowers per terminal apex. Flowers flat and face upright and slightly outward.

*Flower appearance.*—Rounded, orange-colored petals. Flowers are open for about one day before closing. Flowers persistent.

*Flower diameter.*—About 13 cm.

*Flower bud* (*just before showing color*).—Rate of opening: About one or two days depending on temperatures. Length: About 3.4 cm. Diameter: About 1.4 cm. Shape: Elliptic.

*Petals.*—Texture: Smooth, satiny. Arrangement: Corolla consists of five petals that overlap. Shape: Broadly spatulate with rounded apex. Margin: Entire, but slightly ruffled. Length: About 8.1 cm. Width: About 7.2 cm. Color: Upper surface: Orange, 28A; 32A towards apex; fading to close to 23A. Lower surface: Orange, 32A to 31A; fading to close to 24A to 24B; venation and base, yellow, close to 13A. Throat or "eye": Similar to petal, 28A; when petal color fades, "eye" appears darker; glossy.

*Sepals.*—Appearance: Five sepals fused into a star-shaped calyx. Shape: Linear. Texture: Slightly pubescent. Color, outer surface: 146A.

*Bracts.*—Appearance: About six fused as base. Length: About 1.4 cm. Width: About 4 mm. Shape: Linear. Color: 147A.

*Peduncles.*—Length: About 4.75 cm. Diameter: About 3.5 mm at base. Angle: Upright. Strength: Strong, flexible. Texture: Slightly pubescent. Color: Green, 146A.

*Reproductive organs.*—Androecium: Stamen number: Numerous, about 54. Stamen length: About 5 mm. Filament color: 28A. Anther size: About 1 mm by 0.5 mm. Amount of pollen: Abundant. Pollen color: 14A. Gynoecium: Pistil length: About 9.3 cm. Style color: 28A. Stigma appearance: Five, rounded. Stigma diameter: About 2 mm. Stigma color: 46A.

Disease resistance: Resistance to known Hibiscus diseases has not been observed on plants grown under commercial greenhouse conditions.

Seed production: Seed production has not been observed.

It is claimed:

1. A new and distinct Hibiscus plant named 'Caroline', as illustrated and described.

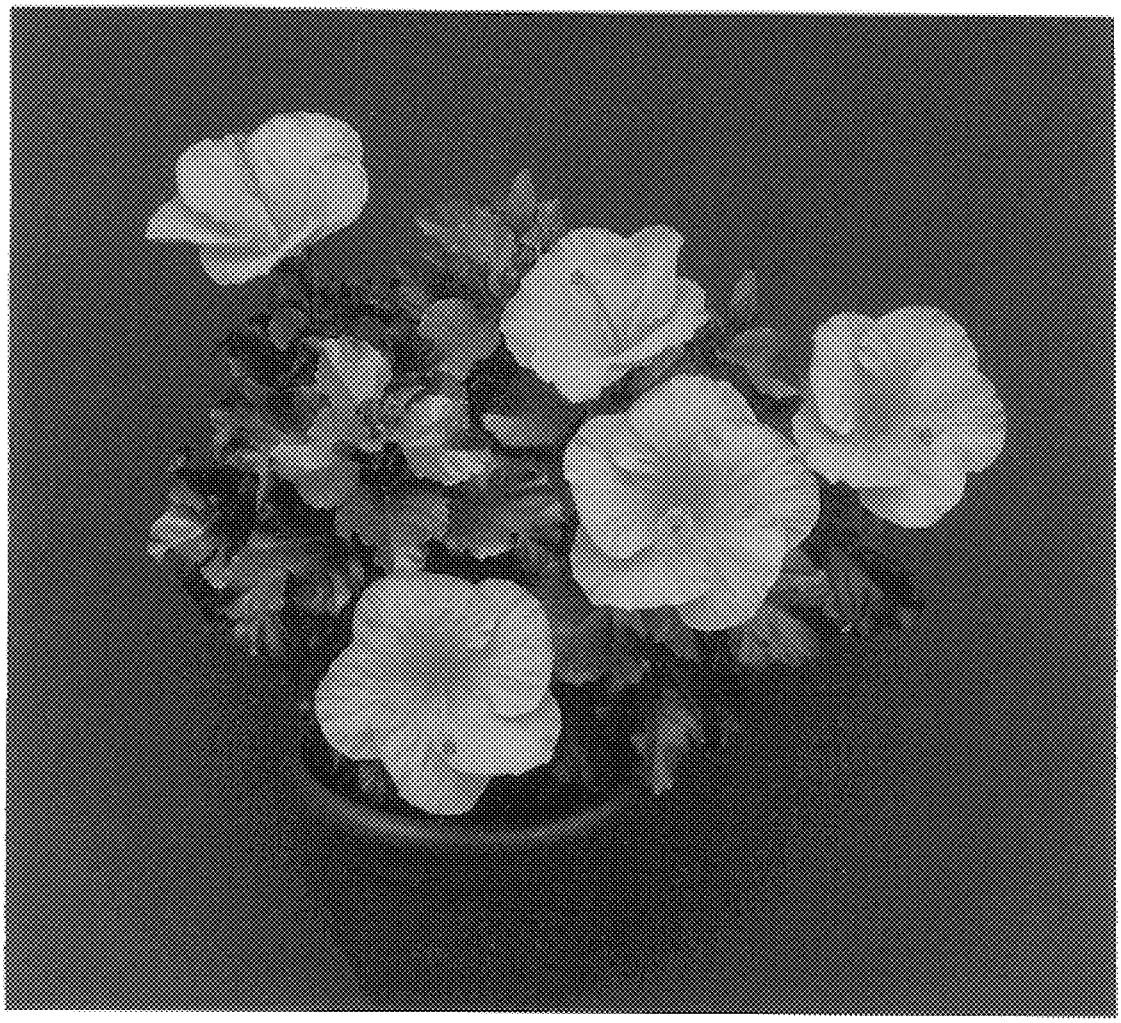

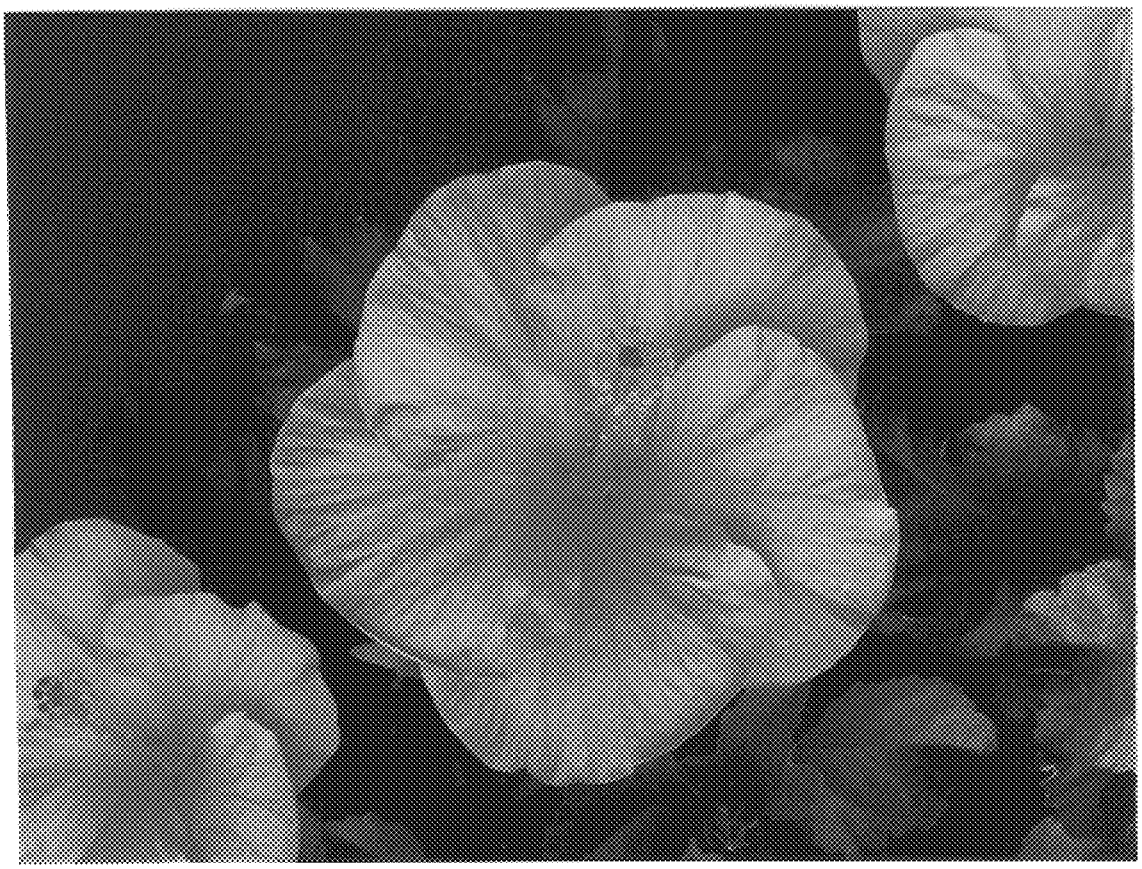

* * * * *